United States Patent
Prasad

(10) Patent No.: US 11,938,100 B2
(45) Date of Patent: Mar. 26, 2024

(54) MICRODAILY-CHILDREN GUMMY FOR OPTIMAL GROWTH, DEVELOPMENT, AND HEALTH

(71) Applicant: Kedar Prasad, San Rafael, NY (US)

(72) Inventor: Kedar Prasad, San Rafael, CA (US)

( * ) Notice: Subject to any disclaimer, the term of this patent is extended or adjusted under 35 U.S.C. 154(b) by 0 days.

(21) Appl. No.: 17/385,611

(22) Filed: Jul. 26, 2021

(65) Prior Publication Data
US 2023/0130604 A1    Apr. 27, 2023

Related U.S. Application Data

(63) Continuation-in-part of application No. 17/359,094, filed on Jun. 25, 2021, now abandoned.

(51) Int. Cl.

| | | |
|---|---|---|
| A61K 31/07 | (2006.01) | |
| A23L 33/105 | (2016.01) | |
| A23L 33/155 | (2016.01) | |
| A23L 33/16 | (2016.01) | |
| A61K 31/015 | (2006.01) | |
| A61K 31/05 | (2006.01) | |
| A61K 31/12 | (2006.01) | |
| A61K 31/122 | (2006.01) | |
| A61K 31/197 | (2006.01) | |
| A61K 31/198 | (2006.01) | |
| A61K 31/352 | (2006.01) | |
| A61K 31/355 | (2006.01) | |
| A61K 31/375 | (2006.01) | |
| A61K 31/385 | (2006.01) | |
| A61K 31/4188 | (2006.01) | |
| A61K 31/4415 | (2006.01) | |
| A61K 31/455 | (2006.01) | |
| A61K 31/51 | (2006.01) | |
| A61K 31/519 | (2006.01) | |
| A61K 31/525 | (2006.01) | |
| A61K 31/593 | (2006.01) | |
| A61K 31/714 | (2006.01) | |
| A61K 33/04 | (2006.01) | |
| A61K 33/06 | (2006.01) | |
| A61K 33/24 | (2019.01) | |
| A61K 33/30 | (2006.01) | |

(52) U.S. Cl.
CPC ............ *A61K 31/07* (2013.01); *A23L 33/105* (2016.08); *A23L 33/155* (2016.08); *A23L 33/16* (2016.08); *A61K 31/015* (2013.01); *A61K 31/05* (2013.01); *A61K 31/12* (2013.01); *A61K 31/122* (2013.01); *A61K 31/197* (2013.01); *A61K 31/198* (2013.01); *A61K 31/352* (2013.01); *A61K 31/355* (2013.01); *A61K 31/375* (2013.01); *A61K 31/385* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/593* (2013.01); *A61K 31/714* (2013.01); *A61K 33/04* (2013.01); *A61K 33/06* (2013.01); *A61K 33/24* (2013.01); *A61K 33/30* (2013.01); *A23V 2002/00* (2013.01)

(58) Field of Classification Search
None
See application file for complete search history.

(56) References Cited

U.S. PATENT DOCUMENTS

2018/0008573 A1*  1/2018  Brown ................. A61K 31/047

OTHER PUBLICATIONS

IVACG (International Vitamin A Consultative Group), Conversion factors for vitamin A and carotenoids, https://pdf.usaid.gov/pdf_docs/Pnacp110.pdf, 2002.*

Ernest Z., Socratic Q&A, How can I convert from international units (IU) to milligrams or micrograms? https://socratic.org/questions/how-can-i-convert-from-international-units-iu-to-milligrams-or-micrograms, 2014.*

* cited by examiner

*Primary Examiner* — Duane Smith
(74) *Attorney, Agent, or Firm* — Dan De La Rosa

(57) ABSTRACT

A formulation comprising at least on vitamin, at least one antioxidant, at least one mineral, at least one plant based nutrient and sodium.

10 Claims, No Drawings

MICRODAILY-CHILDREN GUMMY FOR OPTIMAL GROWTH, DEVELOPMENT, AND HEALTH

PRIORITY DATA

This application is a continuation in part of U.S. application Ser. No. 17/359,094 entitled "Microdaily-EMF-Micronutrients in EMF Radiation Protection" which claims priority off of U.S. Provisional Application No. 62/044,229 entitled "Microdaily-EMF-Micronutrients in EMF Radiation Protection".

BACKGROUND OF THE INVENTION

Most children are deficient in one or more micronutrients. 70% of US children and adolescents have suboptimal deficiency of vitamin D. 9% of them had vitamin D deficiency and 61% of them had insufficiency of vitamin D (1). Secondhand exposure to tobacco smoke induces vitamin D deficiency in 42% of US children (2). Vitamin D deficiency can cause rickets disease, interfere bone growth, increase the risk of heart disease, and cancer (3). Deficiency of vitamin A, vitamin, C, Vitamin D, vitamin E, and folate occurs in American children. 7% American of 6 years and older have deficiency of vitamin C. 16 million are at risk of developing vitamin A deficiency (4).

SUMMARY OF THE INVENTION

Children undergo physical growth and mental development such as cognitive function, emotional, and social skill. Micronutrient requirement is very high in children during this growth period. Even the deficit of one micronutrient can interfere with proper physical and mental development. Micronutrient deficiency may reduce immune function and increase the risk of chronic diseases. Micronutrient deficiency may reduce a child's ability to protect itself from EMF Radiation or other environmental exposures.

Most children are taking excessive amounts of junk foods, sugar rich beverages, and fats. Most children do not participate in physical activity. The above changes in diet and lifestyle leads to obesity as well as inadequate micronutrient intake contribute to micronutrient deficiency in children.

Commercially available multivitamins for children are totally inadequate. For example, none of them have endogenous (body-made antioxidants), such as coenzyme Q10, glutathione-elevating agents (alpha-lipoic acid and N-acetylcysteine), curcumin, resveratrol, quercetin, and selenium. These micronutrients are very important for proper growth and protection against environmental toxins. Other micronutrients, such as vitamin A, vitamin C, vitamin E, vitamin D, and all B-vitamins present at sub-optimal levels. Therefore, these commercial multivitamin formulations are not sufficient to meet the need of children during their growth period. Therefore, I developed Micordaily-EMF for Kids in the form of gummy, which has all ingredients that are missing from the commercial multivitamin gummies for children. In addition, it has two forms of vitamin E (vitamin E succinate and vitamin E acetate). Folate and vitamin B12 are in methylated form. Doses are safe and Effective.

The present invention may allow proper physical growth and mental development, and improve immune function leading to reduced risk of infection.

Why Do Children Need a Daily Vitamin?

Both Children and adults are exposed to the same environmental toxins, including EMF Radiation. However, their needs are in part different.

Adults need adequate micronutrient to maintain healthy body and mind during aging.

Children need adequate micronutrients to ensure proper physical and mental development as well as to maintain them in a healthy condition during growth to adulthood.

Even deficiency in one micronutrient can interfere with physical and mental growth of children.

Factors, which contribute to deficiency include:
Poor diet: lack of fruits and vegetables
Excessive consumption of junk food, fried food, and sugar
Lack of physical activity
Obesity Supplementation with a scientifically prepared mixture of micronutrients together with good diet and physical activity would ensure the proper physical and mental development of children.

Commercially sold gummy vitamins have no endogenous (body-made antioxidants), such as coenzyme Q10, glutathione-elevating agents (alpha-lipoic acid and N-acetylcysteine), curcumin, resveratrol, quercetin, and selenium. They are very important micronutrients for proper growth and protection against environmental toxins. Other micronutrients are at sub-optimal levels.

The present invention maybe administered as a gummy vitamin that has all the ingredients that are missing from commercially sold children gummy vitamins.

It has two forms of vitamin E (vitamin E succinate and vitamin E acetate). The doses are safe and Effective.

It contains Folate and vitamin B12 are in methylated form.

Expected Benefits:

Allows proper physical growth and mental development, improve immune function leading to reduced risk of infection and provide protection from EMF radiation and other environmental exposures.

Reduced hospital visit for children
Reduced absentee from the school for children
Positive interactions for children with teachers and peers
Positive interactions for children with all members of the family In one embodiment, a formulation comprising at least one vitamin, at least one antioxidant, at least one mineral, at least one plant based nutrient and sodium.

In another embodiment a formulation of wherein at least one vitamin is chosen from a group comprising Vitamin A, Vitamin D3, Vitamin B1, Vitamin B2, Vitamin B3, Vitamin B5, Vitamin B6, Vitamin B7, Vitamin B12, Folate and combinations and mixtures thereof.

In yet another embodiment, a formulation of wherein the at least one vitamin is in an amount from about 1 IU to about 10,000 IU.

In still yet another embodiment, a formulation of wherein at least one antioxidant is chosen from a group comprising Vitamin C, D-alpha-tocopherol succinate, D-alpha-tocopherol acetate and combinations and mixtures thereof.

In a further embodiment, a formulation wherein at least one antioxidant is in an amount from about 1 IU to about 10,000 IU.

In still a further embodiment, at least one mineral is chosen from a group comprising calcium, magnesium, zinc, selenium, chromium, and mixtures and combinations thereof.

In another embodiment, a formulation of claim wherein at least on mineral is an amount from about 0.001 mg to about 500 mg.

In yet another embodiment, a formulation wherein at least one plant based nutrient is chosen from a group comprising natural beta carotene, curcumin, trans-resveratrol, quercetin and mixtures and combinations thereof.

In still yet another embodiment, a formulation wherein the plant based nutrient is an amount from about 1 IU to 10,0000 IU.

In another a formulation should be taken at least once a day.

In a further embodiment, a formulation should be taken at least twice a day.

In still a further embodiment, a formulation designed to reduce the harmful effects of environmental factors on human health.

In still yet a further embodiment, a formulation designed to provide protection to humans from environmental factors.

In another embodiment, a formulation of designed to mitigate the harmful effects of environmental factors.

In yet another embodiment, a formulation per serving comprising:
Vitamin A in an amount of about 225 mcg
Vitamin C in an amount of about 25 mg
Vitamin D3 in an amount of about 2.6 mcg
Vitamin E in an amount of about 6 mg
Vitamin E in an amount of about 6 mg
Vitamin B1 in an amount of about 0.75 mg
Vitamin B2 in an amount of about 0.75 mg
Vitamin B3 in an amount of about 6 mg
Vitamin B5 in an amount of about 2.5 mg
Vitamin B6 in an amount of about 0.75 mg
Vitamin B7 in an amount of about 50 mcg
Vitamin B12 in an amount of about 10 mcg
Folate in an amount of about 170 mcg
Zinc in an amount of about 15 mg
Selenium in an amount of about 100 mcg
Chromium in an amount of about 50 mcg
Sodium in an amount of about 4.5 mg
N-acetylcysteine in an amount of about 37 mcg
Coenzyme Q10 in an amount of about 37 mcg
Alpha-lipoic acid in an amount of about 37 mcg
Natural Beta carotene in an amount of about 37 mcg
Curcumin in an amount of about 37 mcg
Trans-resveratrol in an amount of about 37 mcg
Quercetin in an amount of about 37 mcg
Beta-carotene in an amount of about 37 mcg
Sodium in an amount of about 4.5 mg In still another embodiment, a formula comprising:
Vitamin A in an amount from about 1 IU to about 10,000 IU
Vitamin C in an amount from about 1 IU to about 5000 IU
Vitamin D3 in an amount from about 1 IU to about 1200 IU
Vitamin E in an amount from about 1 IU to about 400 IU
Vitamin E in an amount from about 1 IU to about 400 IU
Vitamin B1 in an amount from about 1 mg to about 20 mg
Vitamin B2 in an amount from about 1 mg to about 20 mg
Vitamin B3 in an amount from about 1 mg to about 100 mg
Vitamin B5 in an amount from about 1 mg to about 30 mg
Vitamin B6 in an amount from about 1 mg to about 15 mg
Vitamin B7 in an amount from about 1 mcg to about 500 mcg
Vitamin B12 in an amount from about 1 mcg to about 20 mcg
Folate in an amount from about 1 mcg to about 500 mcg
Zinc in an amount from about 5 mg to about 30 mg
Selenium in an amount from about 10 mcg to about 300 mcg
Chromium in an amount from about 5 mcg to about 100 mcg
N-acetylcysteine in an amount from about 1 mcg to about 300 mcg
Coenzyme Q10 in an amount from about 1 mcg to about 300 mcg
Alpha-lipoic acid in an amount from about 1 mcg to about 300 mcg
Natural Beta carotene in an amount from about 1 mcg to about 300 mcg
Curcumin in an amount from about 1 mcg to about 300 mcg
Trans-resveratrol in an amount from about 1 mcg to about 300 mcg
Quercetin in an amount from about 1 mcg to about 300 mcg
Beta-carotene in an amount from about 1 mcg to about 300 mcg
Sodium in an amount from about 1 mg to about 25 mg In yet another embodiment, a method of manufacturing a formulation by admixing ingredients comprising:
Vitamin A in an amount from about 1 IU to about 10,000 IU
Vitamin C in an amount from about 1 IU to about 5000 IU
Vitamin D3 in an amount from about 1 IU to about 1200 IU
Vitamin E in an amount from about 1 IU to about 400 IU
Vitamin E in an amount from about 1 IU to about 400 IU
Vitamin B1 in an amount from about 1 mg to about 20 mg
Vitamin B2 in an amount from about 1 mg to about 20 mg
Vitamin B3 in an amount from about 1 mg to about 100 mg
Vitamin B5 in an amount from about 1 mg to about 30 mg
Vitamin B6 in an amount from about 1 mg to about 15 mg
Vitamin B7 in an amount from about 1 mcg to about 500 mcg
Vitamin B12 in an amount from about 1 mcg to about 20 mcg
Folate in an amount from about 1 mcg to about 500 mcg
Zinc in an amount from about 5 mg to about 30 mg
Selenium in an amount from about 10 mcg to about 300 mcg
Chromium in an amount from about 5 mcg to about 100 mcg
N-acetylcysteine in an amount from about 1 mcg to about 300 mcg
Coenzyme Q10 in an amount from about 1 mcg to about 300 mcg
Alpha-lipoic acid in an amount from about 1 mcg to about 300 mcg
Natural Beta carotene in an amount from about 1 mcg to about 300 mcg
Curcumin in an amount from about 1 mcg to about 300 mcg
Trans-resveratrol in an amount from about 1 mcg to about 300 mcg
Quercetin in an amount from about 1 mcg to about 300 mcg
Beta-carotene in an amount from about 1 mcg to about 300 mcg
Sodium in an amount from about 1 mg to about 25 mg In even a further embodiment, a method of manufacturing a formulation by admixing ingredients comprising at least one vitamin, at least one antioxidant, at least one mineral, and at least one plant based nutrient.

In yet another embodiment, a method of manufacturing of wherein at least one vitamin is chosen from a group comprising Vitamin A, Vitamin D3, Vitamin B1, Vitamin B2, Vitamin B3, Vitamin B5, Vitamin B6, Vitamin B7, Vitamin B12, Folate and combinations and mixtures thereof.

In still another embodiment, a method of manufacturing of wherein at least one antioxidant is chosen from a group comprising Vitamin C, D-alpha-tocopherol succinate, D-alpha-tocopherol acetate, N-acetylcysteine, Coenzyme Q10, Alpha-lipoic acid, and combinations and mixtures thereof.

In a further embodiment, a method of manufacturing wherein said at least one mineral is chosen from a group comprising calcium, magnesium, zinc, selenium, chromium, and mixtures and combinations thereof.

In still a further embodiment, a method of manufacturing of wherein at least one plant based nutrient is chosen from a group comprising natural beta carotene, curcumin, trans-resveratrol, quercetin and mixtures and combinations thereof.

In recent years, humans are being exposed to increased levels of electromagnetic field (EMF) radiation from devices, such as mobile phones, laptops, and Wi-Fi, microwave ovens, and television sets. Exposure to EMF radiation increased the risk of cancer, non-cancerous diseases, neurological abnormalities, such as electromagnetic hypersensitivity, cognitive dysfunction, and abnormal electroencephalogram (EEG), and damage to reproductive system. EMF radiation exposure also increases the levels of markers of oxidative damage and inflammation that may contribute to the above adverse health effects. There is no effective protective strategy that could reduce EMF radiation damage in humans A few studies showed that treatment with single micronutrient reduced EMF radiation damage in animal models. The use of single micronutrient has produced impressive benefits in reducing the risk of cancer and neurological diseases in animal models, but it has failed to produce similar benefits in such human diseases. In order to avoid this problem associated with the use of a single micronutrient, a comprehensive mixture of micronutrients is proposed for reducing EMF radiation damage in humans.

In one embodiment, a formulation comprising at least on vitamin, at least one antioxidant, at least one mineral, and at least one plant based nutrient.

In one embodiment, a formulation wherein the at least one vitamin is chosen from a group comprising Vitamin A, Vitamin D3, Vitamin B1, Vitamin B2, Vitamin B3, Vitamin B5, Vitamin B6, Vitamin B7, Vitamin B12, Folate and combinations and mixtures thereof.

In one embodiment, a formulation wherein the at least one vitamin is in an amount from about 1 IU to about 10,000 IU.

In one embodiment, a formulation wherein the at least one antioxidant is chosen from a group comprising Vitamin C, D-alpha-tocopherol succinate, D-alpha-tocopherol acetate, N-acetylcysteine, Coenzyme Q10, Alpha-lipoic acid, and combinations and mixtures thereof.

In one embodiment, a formulation wherein the at least one antioxidant is in an amount from about 1 IU to about 10,000 IU.

In one embodiment, a formulation wherein the at least one mineral is chosen from a group comprising calcium, magnesium, zinc, selenium, chromium, and mixtures and combinations thereof.

In one embodiment, a formulation wherein the at least on mineral is an amount from about 0.001 mg to about 500 mg.

In one embodiment, a formulation wherein the at least one plant based nutrient is chosen from a group comprising natural beta carotene, curcumin, trans-resveratrol, quercetin, green tea extract and mixtures and combinations thereof.

In one embodiment, a formulation wherein the at least one plant based nutrient is in an amount from about 5 mg to about 500 mg.

In one embodiment, a formulation should be taken at least once a day.

In one embodiment, a formulation should be taken at least twice a day.

In one embodiment, a formulation is designed to reduce the harmful effects of EMF radiation on human health.

In one embodiment, a formulation is designed to provide protection to humans from EMF radiation.

In one embodiment, a formulation is designed to mitigate the harmful effects of EMF radiation on humans.

In one embodiment, a formulation comprising:
Vitamin A in an amount of about 3000 IU
Vitamin C in an amount of about 1000 mg
Vitamin D3 in an amount of about 800 IU
Vitamin E in an amount of about 200 IU
Vitamin E in an amount of about 200 IU
Vitamin B1 in an amount of about 4 mg
Vitamin B2 in an amount of about 5 mg
Vitamin B3 in an amount of about 30 mg
Vitamin B5 in an amount of about 10 mg
Vitamin B6 in an amount of about 5 mg
Vitamin B7 in an amount of about 200 mcg
Vitamin B12 in an amount of about 10 mcg
Folate in an amount of about 0.4 mg
Calcium in an amount of about 125 mg
Magnesium in an amount of about 75 mg
Zinc in an amount of about 15 mg
Selenium in an amount of about 100 mcg
Chromium in an amount of about 50 mcg
N-acetylcysteine in an amount of about 250 mg
Coenzyme Q10 in an amount of about 30 mg
Alpha-lipoic acid in an amount of about 60 mg
Natural Beta carotene in an amount of about 50 mcg
Curcumin in an amount of about 200 mg
Trans-resveratrol in an amount of about 50 mg
Quercetin in an amount of about 25 mg
Green tea extract in an amount of about 25 mg
In one embodiment, a formulation comprising:
Vitamin A in an amount from about 1000 IU to about 10,000 IU
Vitamin C in an amount from about 200 IU to about 5000 IU
Vitamin D3 in an amount from about 200 IU to about 1200 IU
Vitamin E in an amount from about 50 IU to about 400 IU
Vitamin E in an amount from about 50 IU to about 400 IU
Vitamin B1 in an amount from about 1 mg to about 20 mg
Vitamin B2 in an amount from about 1 mg to about 20 mg
Vitamin B3 in an amount from about 10 mg to about 100 mg
Vitamin B5 in an amount from about 2 mg to about 30 mg
Vitamin B6 in an amount from about 1 mg to about 15 mg
Vitamin B7 in an amount from about 50 mcg to about 500 mcg
Vitamin B12 in an amount from about 2 mcg to about 20 mcg
Folate in an amount from about 0.1 mg to about 2 mg
Calcium in an amount from about 50 mg to about 250 mg
Magnesium in an amount from about 25 mg to about 250 mg Zinc in an amount from about 5 mg to about 30 mg
Selenium in an amount from about 10 mcg to about 300 mcg
Chromium in an amount from about 5 mcg to about 100 mcg
N-acetylcysteine in an amount from about 50 mg to about 500 mg
Coenzyme Q10 in an amount from about 25 mg to about 400 mg
Alpha-lipoic acid in an amount from about 6 mg to about 500 mg
Natural Beta carotene in an amount from about 5 mcg to about 250 mcg RAE
Curcumin in an amount from about 50 mg to about 500 mg
Trans-resveratrol in an amount from about 5 mg to about 250 mg
Quercetin in an amount from about 5 mg to about 200 mg
Green tea extract in an amount from about 5 mg to about 250 mg In one embodiment, a method of manufacturing a formulation by admixing ingredients comprising:
Vitamin A in an amount from about 1000 IU to about 10,000 IU
Vitamin C in an amount from about 200 IU to about 5000 IU
Vitamin D3 in an amount from about 200 IU to about 1200 IU
Vitamin E) in an amount from about 50 IU to about 400 IU
Vitamin E in an amount from about 50 IU to about 400 IU
Vitamin B1 in an amount from about 1 mg to about 20 mg
Vitamin B2 in an amount from about 1 mg to about 20 mg
Vitamin B3 in an amount from about 10 mg to about 100 mg
Vitamin B5 in an amount from about 2 mg to about 30 mg
Vitamin B6 in an amount from about 1 mg to about 15 mg
Vitamin B7 in an amount from about 50 mcg to about 500 mcg
Vitamin B12 in an amount from about 2 mcg to about 20 mcg
Folate in an amount from about 0.1 mg to about 2 mg
Calcium in an amount from about 50 mg to about 250 mg
Magnesium in an amount from about 25 mg to about 250 mg
Zinc in an amount from about 5 mg to about 30 mg
Selenium in an amount from about 10 mcg to about 300 mcg
Chromium in an amount from about 5 mcg to about 100 mcg
N-acetylcysteine in an amount from about 50 mg to about 500 mg
Coenzyme Q10 in an amount from about 25 mg to about 400 mg
Alpha-lipoic acid in an amount from about 6 mg to about 500 mg
Natural Beta carotene in an amount from about 5 mcg to about 250 mcg RAE
Curcumin in an amount from about 50 mg to about 500 mg
Trans-resveratrol in an amount from about 5 mg to about 250 mg
Quercetin in an amount from about 5 mg to about 200 mg
Green tea extract in an amount from about 5 mg to about 250 mg In one embodiment, a method of manufacturing a formulation by admixing ingredients comprising at least on vitamin, at least one antioxidant, at least one mineral, and at least one plant based nutrient.

In one embodiment, a method of manufacturing wherein the at least one vitamin is chosen from a group comprising Vitamin A, Vitamin D3, Vitamin B1, Vitamin B2, Vitamin B3, Vitamin B5, Vitamin B6, Vitamin B7, Vitamin B12, Folate and combinations and mixtures thereof.

In one embodiment, a method of manufacturing wherein the at least one antioxidant is chosen from a group comprising Vitamin C, D-alpha-tocopherol succinate, D-alpha-tocopherol acetate, N-acetylcysteine, Coenzyme Q10, Alpha-lipoic acid, and combinations and mixtures thereof.

In one embodiment, a method of manufacturing wherein the at least one mineral is chosen from a group comprising calcium, magnesium, zinc, selenium, chromium, and mixtures and combinations thereof.

In one embodiment, a method of manufacturing wherein the at least one plant based nutrient is chosen from a group comprising natural beta carotene, curcumin, trans-resveratrol, quercetin, green tea extract and mixtures and combinations thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

As stated above, there is no effective protective strategy for prevention of injury produced by EMF radiation. This invention claimed to solve this problem.

This invention uses a comprehensive mixture of micronutrient, which would reduce acute and long-term adverse health effects of EMF radiation by attenuation oxidative stress and inflammation that contribute to increased risk of cancer, non-cancer diseases, neurological abnormalities, and reproductive system damage.

This invention differs from the use single micronutrient, which cannot protect both aqueous and lipid environment of cells against EMF radiation. A single micronutrient cannot activate Nrf2 as well as increase in dietary and endogenous antioxidants that are required for optimally reducing oxidative and inflammatory damage.

This invention proposes a novel concept of PAMARA (protection as much as reasonably achievable) against EMF radiation by using a comprehensive mixture of micronutrients. No such concept of protection against EMF radiation is available for humans.

On embodiment of the invention discussed here includes Comprehensive Mixture of Micronutrients.

Relationship Between the Components:

A comprehensive mixture of micronutrients contains vitamin A, vitamin C, vitamin E, vitamin D3, beta-carotene, curcumin, resveratrol, conenzyme Q10, green tea extract, quercetin, all B-vitamins, and mineral selenium and zinc.

How the Invention Works:

EMF radiation causes damage by producing excessive amounts of free radicals (increased oxidative stress) and pro-inflammatory cytokines (inflammation). The proposed mixture of micronutrients would decrease oxidative stress and inflammation, and thereby, provide strong protection against EMF radiation damage.

Ionizing radiation such as X-ray or gamma-ray also causes damage by increasing oxidative stress and inflammation similar to those produced by EMF radiation, but at much higher levels than EMF radiation. This invention is based on my previous studies in which a mixture of micronutrients was very effective in reducing damage produced by ionizing radiation such as X-ray and gamma-ray compared to single antioxidant in animal models. In my previous study, a mixture of micronutrients such as proposed here was found to be safe in humans when administered orally.

How to Make Invention

Individual must have done research on the prevention and mitigation of damage produced by ionizing radiation.

This person must have experience in research in micronutrients as well as ionizing radiation.

This individual must have a full understanding of EMF radiation with respect to frequency range in Hz (Hertz), dose of EMF radiation in V/m (voltage/meter), and specific absorption rate (SAR) in W/kg (watt/kilogram).

All proposed antioxidants, B-vitamins, and minerals are essential for an optimal protection against EMF radiation damage. Iron, copper, manganese, and heavy metals are excluded.

Vitamin E should be in the form of d-alpha-tocopheryl succinate, vitamin A in the form of retinal palmitate, and vitamin C in the form of calcium ascorbate. All vitamin E and beta-carotene should be in natural form.

This person must be aware of the research, which show that iron, copper and manganese interact with vitamin C to generate extensive amounts of free radicals. Humans have no significant mechanisms of eliminating these trace minerals. Increased body store of one of these trace minerals enhances the risk of chronic diseases. Also, increased accumulation of heavy metals in the body could be neurotoxic. The body has method of elimination of minerals or heavy metals.

How to Use Invention

The proposed mixture of micronutrients is manufactured in the form of 6 capsules. Take orally 3 capsules in the morning with a meal and 3 capsules in the evening with a meal. Twice a day is recommended in order to maintain steady levels of micronutrients in the body.

EMF radiation increases the risk of acute and chronic adverse health effects by producing excessive amounts of free radicals and inflammation. because of limitations of using a single antioxidant in humans, a mixture of micronutrients for protection against EMF (electromagnetic field) radiation damage is disclosed. Supplementation with this micronutrient mixture may reduce the risk of cancer, non-cancerous diseases, neurological abnormalities, and reproductive system damage produced by exposure to EMF radiation.

A document in support of the proposed mixture of micronutrients, which would protect against acute adverse health effects of EMF radiation is presented here.

Detailed Description of the Invention

The advent of wireless communication technologies has lead to increased exposure EMF radiation that has enhanced risk of adverse health effects in humans. Introduction of 5G or 5th Generation wireless technology, which transmits signal at much higher frequency range (3-300 GHz) than previous Generations, has raised further concerns about its impact on human health. No human studies on the effect of 5G infrastructures involving numerous antennae located in your neighborhood have been performed. Most epidemiologic studies showed that EMF radiation emitted from previous Generation's frequencies increased the risk of cancer in humans. Since extensive animal studies, and mechanistic studies in which EMF radiation increases the levels of markers of oxidative stress and inflammation, the above human studies can be considered valid. However, a few epidemiologic investigations have reported no increase in cancer risk following exposure to EMF radiation. The inconsistent epidemiologic studies on cancer risk could be due to the fact that the level of frequency, dose (strength) (voltage per meter or V/m), intensity (millitesla or mT), and SAR (specific absorption rate, Watts/Kg or W/Kg of tissue) were not comparable. Supplementation with individual antioxidants has reduced oxidative stress and protected against EMF radiation-induced damage. Because of limitations in implementing physical protection, a biological strategy for tissue protection should be developed. The major objectives of this review are to briefly describe (a) biological responses of 5G frequency range, (b) EMF radiation-induced cancer risk, and neurological and non-neurological damage, (c) the role of increased oxidative stress and inflammation in such damage, and (d) identify gaps in the knowledge. The review proposes a novel concept of PAMARA (protection as much as reasonable achievable) using a mixture of micronutrients for tissue protection against EMF radiation-induced damage.

During the course of evolution, humans haves been exposed to background ionizing, non-ionizing radiation such as ultraviolet radiation and naturally occurring non-polarized EMF radiation. In recent years, they are being exposed to increased levels of man-made polarized electromagnetic field (EMF) radiation from devices, such as mobile phones, laptops, and Wi-Fi, microwave ovens, and television sets. Non-polarized EMF radiation cannot induce oscillation or vibrations in charged molecules such as Na, K Ca and others, whereas polarized EMF radiation induced such vibration (1). The magnitude of vibrations of charged molecules depends upon the frequency of EMF radiation. Such vibration of charged molecules in the body can interfere with electrical communications between cells, especially in the brain and heart. Therefore, Polarized EMF radiation induced vibration of charged particles in the body may represents on of the mechanisms that can increase health risks in humans. EMF radiation has been classified into extremely low frequency EMF (ELF-EMF), which has a frequency range up to 300 Hz, and radio frequency EMF (RF-EMF) with a frequency range of 3 KHz to 300 GHz) (2).

The introduction of 5G or 5th Generation, the latest wireless technology, which transmits signal at frequency range between 30-300 GHz, has alarmed many health professionals and public because of its impact on increased adverse health effects in humans. There are some major differences between 5th Generation and previous generations technology. 5G utilizes millimeter waves (also called millimeter bands or extremely high frequency) and higher frequencies than the previous generations technologies. 5G EMF radiation can increase the risk of cancer, genetic damage, learning and memory deficits, and other neurological disorders, The health effects of 5G frequency on humans have not been investigated. Most epidemiologic studies suggest that EMF radiation may increase the risk of cancer in humans (3-6). Animal studies supported the above conclusion (7-10). A few epidemiologic studies have reported no increase in cancer risk (11-14). The potential reasons for the above inconsistent results in humans are discussed later in this review.

Exposure to EMF radiation induced neurological abnormalities in some individuals, such as electromagnetic hypersensitivity, cognitive dysfunction, and abnormal electroencephalogram (EEG) (15-20). It also caused non-neurological damage such as rise in blood pressure (21), and endocrine changes, sperm and testicular damage, ocular damage, and calcium overload (22). The exact mechanisms of EMF-induced these damages remain to be investigated.

Cell culture studies revealed that exposure to EMF radiation decreased the viability of cells, and increases chromosomal damage and double-strand DNA breaks (23-27). The changes in gene expression especially related to cancer, neurological and non-neurological diseases following exposure to EMF radiation have not been studied either on neuronal or non-neuronal cell culture.

Exposure to EMF radiation increased the levels of markers of oxidative damage in animals (13, 28-30) and humans (31-35) and inflammation in animals (36-42). No studies on the levels of markers of inflammation in the blood of humans are available. Such studies should be conducted with appropriate attention to dose (V/m), intensity (mT), and energy absorption (SAR, W/kg).

Since EMF radiation increases oxidative stress and inflammation, supplementation with antioxidants could reduce these cellular deficits. Indeed, a few studies showed that individual micronutrients before exposure to EMF radiation reduced adverse health effects in animal and cell culture models (29, 32, 33, 39, 43-46). No significant studies on the effects of administration of single or multiple micronutrients administered before exposure to EMF have been performed in humans.

At present, there are no guidelines for tissue protection against EMF radiation-induced damage in humans. For protection against ionizing radiation (x-ray or gamma-ray), we have proposed a novel concept of tissue protection with a mixture of micronutrients (47), but no specific recommendations were made in this study.

The major objectives of this review are to briefly describe (a) biological responses of 5G frequency range, (b) EMF radiation-induced cancer risk, and neurological and non-neurological damage, (c) the role of increased oxidative stress and inflammation in such damage, and (d) identify gaps in the knowledge. The review proposes a novel concept of PAMARA (protection as much as reasonable achievable) using a mixture of micronutrients for tissue protection against EMF radiation.

Biological Responses to 5G Frequency Range

This 5G technology uses millimeter-wave, also known as extremely high frequency (EHF) wave, which transmits signal at frequency between 30 GHz-300 GHz. These frequencies are called millimeter waves because they have wavelengths between 1 mm and 10 mm, whereas radiowaves transmit signal at frequency between 3 KHz to 300 GHz, and have longer wavelengths in centimeter.

The effects of millimeter wave on human health compared to radio wave have not been adequately investigated. A review of several studies revealed that millimeter waves increase skin temperature, alter gene expression, promote cell proliferation and synthesis of proteins linked with oxidative stress, and inflammatory responses. These changes could damage eye and neuromuscular activity (48). Another review analyzed 94 publications in vivo and in vitro on the health impact following exposure to frequency range between 6-100 GHZ). Eighty percent of the in vivo studies showed biological responses following exposure to EMF radiation, while 58% of the in vitro studies showed such responses. In vivo criteria of biological responses included alteration in physiological, neurological and histology parameters, whereas in vitro biological responses included changes in gene expression and protein synthesis, and enhanced cytotoxic effects, genotoxic effects, and temperature-related reactions (49). Operating frequency ranges of currently used wireless communication devices are presented in Table 1 below.

TABLE 1

Operating frequencies range of currently used wireless devices

| Types of devices | Frequency range |
| --- | --- |
| RF-EMF radiation | 3 KHz-300 GHz |
| EL-EMF radiation | 0-300 Hz |
| 5 G | 3-300 GHz |
| 4G | 2-8 GHz |
| 3G | 1885-2200 MHz |
| 2G | 800-1900 MHz |
| 1G | 450 MHz |
| WI-FI | 2.4 GHz |
| Mobil phone models | 1800-2200 MHz |
| Laptops | 1000-3600 MHz |

G = Generation
RF-EMF = Radiofrequency -Electromagnetic field. Transfer of energy by radiowaves
ELF-EMF = Extremely low frequency-electromagnetic field Effects of EMF Radiation on Cancer Risk
Human Studies:

In 2011, an expert working group of the International Agency for Research on Cancer (IARC) defined RF-EMF radiation emitted from mobile phones or other wireless devices as Group 2B ("possible") human carcinogen (50). Several epidemiologic studies suggest that exposure to EMF radiation enhances the risk of glioma, acoustic neuroma, and meningioma. Ipsilateral use of mobile phone showed higher risk of these brain tumors on the side used than on the contralateral side. An elevated risk of these cancers tends to enhance with increasing latency, time of use, and with first exposure at the age 20 years and younger (3-5). Young women aged 21-39 years who were exposed to EMF radiation emitted from the Cell Phone kept in their brassieres at the rate of 10 h/day for several years developed excess incidence of multifocal invasive cancer in the area of the breast immediately adjacent to the cell phone (6).

A few studies have reported no effect of EMF radiation emitted from mobile phones (11, 12). The use of mobile Phone by children and adolescents did not increase the incidence of brain tumors (51). The adult users of cellular phones and cordless phones did not show enhanced the risk of glioma or meningioma (52, 53). Exposure to RF-EMF radiation did not increase the risk of brain cancer (glioma and meningioma) (14).

Animal Studies:

The US National Toxicology Program (NTP) has conducted comprehensive studies on the effects of EMF radiation exposure with 900 MHz in rats and with 1900 MHz in mice during pregnancy and during the entire lifespan of offspring on the incidence of cancer. These investigations showed that increased incidence of tumor, especially glioma and malignant schwannoma occur primarily in the cardiac nerves, but also in the brain. In addition, evidence of DNA damage was present in these organs (7-9). The results of these studies were questioned by the ICNIRP (International Commission on Non-Ionizing Radiation Protection) (54). However NTP studies were supported by the Ramazzini Institute's investigations, which show that exposure to EMF radiation with 1800 MHz at the highest dose of 50 V/m (volts/meter) increased the incidence of tumor of the brain and heart in rats (10).

Some potential reasons for inconsistent epidemiologic investigations on cancer risk in humans following exposure to EMF radiation are discussed here. The health effects of EMF radiation depends upon the level of frequency, dose (strength) (voltage per meter or V/m), intensity (millitesla or mT), and energy absorption SAR (specific absorption rate, Watts/Kg of tissue). Higher the frequency, strength, intensity, and energy absorption greater would be the damage (10). Among these factors, the amount of energy absorption (SAR) is most critical in determining the extent of damage. These variables can easily be controlled in animal or cell culture studies, but it is very difficult to control them in human epidemiologic investigations. This difficulty may account for the controversy regarding EMF radiation-induced increase in cancer risk. Since epidemiologic studies on EMF radiation-induced cancer risk are supported by the animal studies and by the cellular mechanisms that participate in carcinogenesis processes, EMF radiation-induced cancer in humans is a valid conclusion.

Effects of EMF Radiation on Neurological Abnormalities
EMF Radiation-Induced Hypersensitivity:

A review has described an early history of EMF-hypersensitivity. As early as in 1970, a study from the former Soviet Union described the "microwave syndrome" among military personnel, who were working with radio and radar equipments. This syndrome included fatigue, dizziness, headache, and inability to focus, cognitive impairment, and sleep disturbances. Similar symptoms were reported among Swedes employees, who worked in front of cathode ray tube monitors. Additional symptoms included flushing, burning, and tingling of the skin especially on the face, and photosensitivity. Similar symptoms were also reported from Finland following exposure to EMF radiation (15). EMF radiation-induced electromagnetic hypersensitivity is now referred to as idiopathic environmental intolerance (IET) or electrohypersensitivity (EHS). The prevalence of EMF radiation hypersensitivity was 5-30% for mild cases, 1.5% to 5% for moderate cases, and 1.5% for severe cases. The prevalence of electromagnetic hypersensitivity was 1.55% in Sweden (15) and 13.3% that decreased to 4.6% over 5 years period in Taiwan (16).

Patients with hypersensitivity showed neurological symptoms that include headache, tinnitus, hyperacusis, dizziness, balance disorder, fibromyalgia, vegetative nerve dysfunction, and reduced cognitive capability, immediate memory loss, attention deficits, and eventually tempo-spatial confusion. These symptoms were associated with chronic insomnia, fatigue, depressive tendency, anxiety emotional problem, and irritability (17, 18).

The International Commission of Non-Ionizing Radiation Protection Report showed that daily to RF-EMF radiation form cell phones more than 50 minutes might increase the risk of early dementia or other thermal damage (19). Power plant workers, who were exposed to ELF-EMF radiation exhibited poor sleep quality, increased stress, depression, and anxiety (20). Swiss adolescents exposed to RF-EMF radiation in their head area exhibited decreased memory scores (verbal memory) (55).

Exposure to mobile phone-EMF radiation for only 5-min impaired working memory, which was greater in 60 years or older individuals as well as in those who had mild cognitive impairment compared to healthy participants (56).

EMF-radiation-induced increases in alpha band of electroencephalogram (EEG) were related to a rise in cerebral temperature in humans (57). Short-term exposure to RF-EMF radiation reduced EEG alpha power, but had no impact on cognitive function (58). Additional human studies are needed to define EMF radiation-induced biochemical and genetic changes that leads to electromagnetic hypersensitivity, cognitive dysfunction, and depression.

Mice exposed to 835 MHz EMF radiation at absorption of energy rate SAR (specific absorption rate) of 4.0 W/Kg of tissue exhibited increased autophagy, hyperactivity, and demyelination in the cortical neurons (59). Exposure to 900 MHz for 1 h per day for the entire adolescent period showed loss of pyramidal neurons in the hippocampus, and an increase in the levels of melondialdehyde and a decrease in catalase levels in rats. This suggests that EMF radiation-induced damage to the hippocampus was related to increased oxidative stress (30).

Neurons are electrically charged and exchange information with other neurons electronically. This is one of the mechanisms by which neurons conduct their normal function. EMF radiation alters this mechanism of communication that could induce damage to nerve cell function. Another method of communication between neurons is mediated by biochemical compounds.

Effects of EMF Radiation on Non-Neoplastic and Non-Neurological Damage

A review of several studies on the effects of EMF radiation from Wi-Fi reported that such exposure caused increased oxidative stress, sperm/testicular damage, neuropsychiatric effects including EEG changes, apoptosis, DNA damage, endocrine changes, and calcium overload (22). Exposure of reproductive system to EMF radiation emitted by GSM (global System for Mobile Communication), which has frequency range of 2G and 2.5G, increased production of free radicals by increasing the activity of reduced nicotinamide adenine dinucleotide (NADH) oxidase in the cell membrane (60). Female rats exposed to 1800 MHz caused eye damage by upregulating the expression of caspase-2 and P38MAPK (p38 mitogen-activated protein kinase) in ocular cells (61).

Workers using mobile phones for 60 minutes showed increased systolic blood pressure compared to those who spent less time talking on the cell phones. Occupational stress tends to enhance further the levels of systolic blood pressure. The study further revealed that men exposed EMF radiation showed an excess of blood pressure abnormalities, whereas women revealed more impairment of the ECG (electrocardiogram) profile (21). Additional investigations with larger sample size to evaluate the effect of EMF radiation on blood pressure are needed.

Effects of EMF Radiation on Cellular Damage

Human peripheral blood lymphocytes were programmed to enter mitosis and then exposed to EMF radiation of 3G frequencies during the G2 phase of the cell cycle. The results showed that irradiated lymphocytes exhibited increased chromatid-type aberrations (gaps and breaks) an excess of up to 275% compared to unirradiated controls (23). Mouse spermatocyte cells (GC-2 cell line) were exposed to ELF-EMF radiation (50 Hz) intermittently (5 min on and 10 min off) at an intensity of 1, 2, or 3 millitesla (mT) or RF-EMF radiation (1800 MHz) at the specific absorption rate (SAR) of 1, 2, or 4 W/kg (watts/kg of tissue) for 24 hours. The results showed that neither ELF-EMF nor RF-EMF radiation affected the viability of cells. However, ELF-EMF radiation at the highest intensity of 3 mT increased double-strand DNA breaks, but RF-EMF did not. Furthermore, RF-EMF exposure at SAR of 4 W/kg increased oxidative damage to DNA bases, but exposure to ELF-EMF did not. Thus, both ELF-EMF and RF-EMF exposures caused DNA damage, which was dependent upon intensity and energy absorption, respectively (24). Mouse macrophages exposed to ELF-EMF with frequency of 50 Hz at the intensity of 1.0 millitesla (1 mT) did not increase micronuclei formation, however, it enhanced the phagocytic activity of these cells (25).

A review has reported that individuals exposed to EMF radiation exhibited enhanced chromosomal damage in their lymphocytes or exfoliated buccal cells (26). However, one study found that mobile phone-EMF radiation exposure did not affect the levels of micronuclei in exfoliated buccal cells in humans (62). EMF radiation emitted from the cell phone induced DNA damage in the hair follicles in the ear canal. The levels of DNA damage were increased with daily increase in exposure time (27).

A few studies showed that EMF radiation produced no adverse effects (63-66). The reasons for these studies showing no adverse health effects of EMF radiations are not known. These studies have utilized different frequencies, dose (v/m), intensity (mT), and specific absorption rate in W/Kg, which may account for the above inconsistent results.

EMF Radiation Increases Oxidative Stress
Human Studies:

A review has proposed that EMF radiation enhances production of mitochondria-generated free radicals in the reproductive systems of both men and women (31). High-voltage electricity generates ELF-EMF. Workers, who were chronically exposed to ELF-EMF, had elevated urine levels of 8-hydroxy-2-deoxy guanosine (8-OHdG) and F2-isoprostane compared to control groups (33). Oxidative stress following exposure to either ELF-EMF or RF-EMF radiation together with impaired DNA repair processes, repair mechanism, and other cellular damages can elevate the risk of development of cancer (34).

Exposure to ELF-EMF radiation emitted from high-voltage power lines increased oxidative stress as evidenced by elevated levels of urinary 8-isopsrostane and 8-hydroxy-deoxy guanosine in workers (32). However, an investigation of the effects of ELF-EMF radiation did not show increased oxidative stress in workers performing tour-inspection near transformers and distribution power lines (35).

Animal Studies:

Exposure of immature and mature rats with 900 MHz 2 h/day for 45 days increased oxidative damage as evidenced by decreased glutathione levels and antioxidant enzyme activity, and increased levels of lipid peroxidation and nitric oxide in lymphoid organs. Immature rats showed higher levels of oxidative stress than mature rats (13). Acute exposure with ELF-EMF radiation increased oxidative stress in the brain as suggested by reduced activities of antioxidant enzymes catalase and superoxide dismutase in adult male rats, while it did not influence the levels of stress hormone corticosterone (28). Exposure of rat lymphocytes with 930 MHz at a SAR (specific absorption rate) rate of 1.5 W/kg did not change basal intracellular levels of free radicals; however, it enhanced the production of free radicals generated by $FeCl_2$ (ferrous chloride) (67). Rats exposed to 900 MHz for 30 min/day for 10 days showed increased oxidative damage in the kidney as evidenced by increased levels of MDA and decreased activities of antioxidant enzymes superoxide dismutase, catalase, and glutathione peroxidase (29). Continuous exposure with EMF radiation of 900 MHz for 1 h throughout adolescent period increased oxidative damage in the sciatic nerve cells of male rats (68). Male rats exposed to 1966.1 MHz at dose of 4 $mV/cm^2$ and SAR of 0.36 W/kg showed increased levels of oxidative stress, inflammation markers (IL-1beta, IL-6, and TNF-alpha compared to control animals. In addition, increased weight of adrenal gland and enhanced levels of stress hormones (adrenocorticotropic hormone and corticosterone were observed compared to controls (69). Exposure to 900 MHz and 1800 MHz induced significant increase in lipid peroxidation and reduction in level of glutathione in the testis and epididymis. Although no difference was found in total sperm count, sperm motility was significantly reduced, causing impaired fertility in animals exposed to EMF radiation (70).

EMF Radiation Enhances Chronic Inflammation
Animals Exposed to 1800 MHz:

Rats with lipopolysaccharide (LPS)-induced neuroinflammation were exposed to head only with 1800 MHz EMF radiation for 2 hrs at a specific absorption rate of 1.55 W/kg. Levels of neuroinflammation induced by LPS were further enhanced in the auditory cortex concomitant with increased growth of microglia processes and reduced firing rates. In addition, a larger proportion of auditory cortex locations had high acoustic thresholds. However, these changes were not observed in animals not treated with LPS. This suggests that 2-hour exposure to mobile cell phone operating on a frequency of 1800 MHz does not induce inflammation in normal rats but that a second stressor may be needed (36). Experiments performed under similar experimental condition with an increased SAR (specific absorption rate) of 2.9 W/kg also aggravated LPS-induced inflammation in the cerebral cortex (37). Exposure to EMF radiation with 900 MHz 45 min/day at an average specific absorption rate of 1.5 W/kg or 15 min/day at an average specific absorption rate of 6 W/kg emitted by mobile phones increased the levels of glial fibrillary acidic protein (GFAP), a marker of gliosis in the brain of rats (38). EMF radiation enhanced secretion pro-inflammatory cytokines (TNF-alpha, IL-1 beta, and IL-6), and production of nitric oxide (NO), and reduced phagocytic activity of microglia cells (39). Exposure of microglia cells in culture (N9 microglia cells) to EMF radiation activated Janus kinase 2 (JAK2) and Signal Transducer and Activator of Transcription Protein-3 (STAT3) and enhanced binding ability of STAT3 to DNA. In addition, exposure to EMF radiation markedly increased the expression of markers of inflammation (CD11b, TNF-alpha, and iNOS) and production of NO. Treatment with pyridone 6, an inhibitor of JAK2, suppressed EMF radiation induced inflammatory responses (71).

Animals Exposed to 900 MHz

A 15 minute exposure to 900 MHZ from mobile phone at a SAR (specific absorption rate) of 6 W/kg activated glia cells as evidenced by increased levels of glial fibrillary acidic protein (GFAP) in a time-dependent manner in adult rat (40); however, it failed to produce similar effects in older rats, suggesting that the effect of EMF radiation of frequency of 900 MHz is age-dependent (41). EMF radiation emitted from mobile phone impaired immune function in rats. But this effect was mitigated by supplementation with vitamin D (72). Exposure to EMF radiation with 900 MHz in rats with elevated lipopolysaccharides-induced neuroinflammation during gestation or during adolescent did not influence behavior or further increase in inflammation in the brain (42). No studies on the levels of markers of inflammation in the blood of humans are available. Such studies should be conducted with appropriate attention to dose in V/m and specific absorption rate in W/kg).

How to Protect Human Tissues Against EMF Radiation and Other Harmful Environmental Factors Physical Protection Suggestions It is difficult to develop guidelines, because EMF radiation at varying levels is present all around in the environment, houses, and workplaces. US Federal Trade Commission Consumer Information report suggests that increasing distance between EMF radiation source and recipient, reducing exposure time to EMF radiation, and shielding. These principles would be effective in reducing the dose of EMF radiation, if there is a single source of EMF radiation. However, there are multiple sources of EMF radiation therefore, these principles are difficult to implement. The claims of effectiveness of shielding products made by the commercial companies are false (73, 74). In addition, Federal Trade Commission report suggests that shielding may interfere with the cell phone signal, causing it to draw even more power in order to communicate with the cell phone tower (also called base station), probably exposing individuals to more EMF radiation. Because of limitations of utilizing the principles of physical protection against EMF radiation, it is essential that a biological strategy for tissue protection should be developed.

Biological Protection with Micronutrients

Since EMF radiation increases oxidative stress and chronic inflammation, which contribute to EMF radiation-induced damage, effects of micronutrients on reducing the tissue damage were investigated. Most such studies were conducted with a single micronutrient. These studies are described here.

Human Studies

Resvertarol and Green Tea:

Workers, who are chronically exposed to ELF-EMF radiation from high voltage electricity exhibited increased oxidative stress. Treatment with resveratrol reduced this damage (33). Supplementation with green tea polyphenol reduced ELF-EMF radiation-induced oxidative stress in individuals working near the high-voltage power plants (32).

Animal Studies

Melatonin and Omega-3-Fatty Acids:

Melatonin treatment prevented EMF radiation (900 MHz) induced oxidative damage in the kidney of rats (29). Prenatal exposure to 900 MHz EMF radiation together with melatonin or omega-3-fatty acids prevented EMF radiation-induced neuronal damage in the hippocampus of rats (43).

Luteolin:

Rats exposed to 900 MHz radiation showed reduced number of lending cells, primary spermatocytes, and spermatids compared to control animals. Treatment of animals with luteolin, a naturally occurring flavonoid with antioxidant and anti-inflammatory activity, enhanced the number of these cells compared to EMF irradiated animals not receiving luteolin (44).

Garlic Powder:

Exposure to 900 MHz at the average specific absorption rate of 1.08 for 1 h/day for 3 weeks increased the levels of MDA and advanced oxidation protein production in the brain; however, treatment with garlic powder, which exhibits antioxidant and anti-inflammation activities, reduced oxidative damage in the brain of rats (75).

Folic Acid:

Exposure to RF-EMF radiation of 900 MHz 60 min/day for 21 days caused reduction in the number of total pyramidal and granular cells in the hippocampus and dentate gyres and Purkinje cell number in the cerebellum of rat. Treatment with folic acid decreased these changes in the hippocampus and cerebellum (76).

Cell Culture Studies

Curcumin:

Curcumin treatment of microglia cells in culture prevented EMF-induced elevation of pro-inflammatory cytokines and reduced phagocytic activity (39).

Vitamin A:

Exposure of porcine blood platelets to 1 KHz frequency emitted from liquid-crystal-display monitors at the intensity of 220 V/m for 30 and 60 minutes increased the levels of malondialdehyde (MDA); however, treatment with vitamin A significantly attenuated such changes (46).

Selenium:

Human embryonic kidney cells (HEK293) exposed to 2.4 GHz EMF radiation for 1 h revealed increased levels of MDA and decreased activities of superoxide dismutase (SOD) and glutathione peroxidase. In addition, the levels of apoptosis and caspase-3 activity were higher and Bcl2 were lower in EMF irradiated cells compared to controls. Treatment of these cells before EMF radiation exposure with selenium reduced such EMF radiation-induced biochemical changes (45).

The above limited studies show that micronutrients including antioxidants can reduce oxidative stress and reduce damage mostly in animal studies. Additional studies with individual and multiple micronutrients on reducing EMF radiation-induced damage should be performed. In a mean while, it is unlikely that a single micronutrient would be able to provide any significant protection in humans.

Limitations of Using Single Antioxidant in Protecting Against EMF Radiation Damage Although individual micronutrient has produced some benefits in experimental systems, it is unlikely that such an approach would be useful in reducing EMF radiation-induced damage in humans. The potential reasons include (a) different antioxidants are distributed differently in the subcellular compartments of cells; therefore, a single antioxidant cannot protect all parts of the cell; (b) administered single antioxidant in a high internal oxidative environment of EMF radiation exposed individuals becomes oxidized and then acts as a pro-oxidant; (c) an elevation of the levels of antioxidant enzymes and dietary and endogenous antioxidants is essential for reducing oxidative stress and inflammation, a single micronutrient cannot achieve this; (d) the affinity of different antioxidants for free radicals differs, depending upon their solubility; (e) both the aqueous and lipid compartments of the cell need to be protected together; a single antioxidant cannot meet this goal; (f) vitamin E is more effective in quenching free radicals in a reduced oxygenated cellular environment, whereas vitamin C and alpha-tocopherol are more effective in a higher oxygenated environment of the cells (77); (g) vitamin C is important for recycling the oxidized form of alpha-tocopherol to the antioxidant form (78); (h) different antioxidants alters the expression of different microRNAs each of which guides its respective mRNA to produce only protective proteins (79). For example, some antioxidants can activate Nrf2 by upregulating miR-200a that inhibits its target protein Keap 1, whereas others activate Nrf2 by downregulating miR-21 that binds with 3-UTR Nrf2 mRNA (80).

Evidence for Failure of a Single Antioxidant in Human Studies

Supplementation with a single antioxidant in humans did not produce those benefits that were observed in animal models. For examples, administration of beta-carotene alone increased the risk of lung cancer in male heavy smokers (81). Vitamin E treatment was ineffective in patients with Alzheimer's disease, but it reduced the rate of decline in cognitive function in early phase of this disease (82, 83). Vitamin E was ineffective in heart disease on primary and most secondary outcomes (84). Thus, it is unlikely that the use of single antioxidant would significantly reduce EMF radiation-induced damage.

Evidence for the Usefulness of a Mixture of Micronutrient in Human Studies

Supplementation with a mixture of micronutrients produced beneficial effects in two clinical studies. For example, administration of multiple micronutrients reduced the risk of cancer in men (85) and prolonged the time period for initiating the anti-viral therapy in HIV infected patients (86). Therefore, it is highly likelihood that proposed mixture would be effective in reducing acute and late adverse health effects following exposure to EMF radiation.

Proposed Concept of PAMARA (Protection as Much as Reasonable Achievable) for EMF Radiation Protection A novel biological concept PAMARA for tissue protection against EMF radiation damage is proposed. This concept suggests that administration of a mixture of micronutrients to individuals who are likely to receive EMF radiation doses may reduce its adverse health effects. A mixture of micronutrients containing vitamin A, mixed carotenoids, vitamin C, alpha-tocopheryl acetate, alpha-tocopheryl succinate, vitamin D3, alpha-lipoic acid, n-acetyl-cysteine, coenzyme Q10, omega-3-fatty acids, curcumin, resveratrol, quercetin, green tea extract, all B-vitamins, selenomethionine, and zinc is proposed. This mixture would increase the levels of antioxidant enzymes by activating a nuclear transcriptional factor Nrf2 and the levels of dietary and endogenous antioxidant compounds. These cellular changes are essential for optimal tissue protection against EMF radiation-induced damage. The formulation for the proposed mixture of micronutrients is provided in Table 2 and the dose range of each micronutrient is presented in Table 3.

TABLE 2

Microdaily-EMF formula

| Doses of ingredients | Dose per day |
| --- | --- |
| Vitamin A (as palmitate) | 3000 IU (900 mcg) |
| Vitamin C (as calcium ascorbate, 80% vitamin C,9.4% Ca) | 1000 mg |
| Vitamin D3 (as cholecalciferol) | 800 IU (10 mcg) |
| Vitamin E (as D-alpha-tocopherol succinate) | 200 IU (132 mg) |
| Vitamin E (as D-alpha-tocopherol acetate) | 200 IU (132 Mg) |
| Vitamin B1 (as thiamine mononitrate) | 4 mg |
| Vitamin B2 (as riboflavin) | 5 mg |
| Vitamin B3 (as niacinamide) | 30 mg |
| Vitamin B5 (as d-calcium pantothenate) | 10 mg |
| Vitamin B6 (as pyridoxin HQ) | 5 mg |
| Vitamin B7 (Biotin) | 200 mcg |
| Vitamin B12 (as methylcobalamine) | 10 mcg |
| Folate (as L-5- methyltetrahydrofolate, calcium) | 0.4 mg |
| Calcium (as citrate) | 125 mg |
| Magnesium (as citrate) | 75 mg |
| Zinc (as biglycinate chelate) | 15 mg |
| Selenium (as selenomethionine) | 100 mcg |
| Chromium (as picolinate) | 50 mcg |
| N-acetylcysteine | 250 mg |
| Coenzyme Q10 | 30 mg |
| Alpha-lipoic acid | 60 mg |
| Natural Beta carotene | 50 mcg RAE |
| Curcumin | 200 mg |
| Trans-resveratrol | 50 mg |
| Quercetin | 25 mg |
| Green tea extract | 25 mg |

TABLE 3

Microdaily-EMF formula

| Dose range of Ingredients | Dose per day |
| --- | --- |
| Vitamin A (as palmitate) | 1-10,00 IU |
| Vitamin C (as calcium ascorbate, 80% vitamin C,9.4% Ca) | 1-5000IU |
| Vitamin D3 (as cholecalciferol) | 1-1200IU |
| Vitamin E (as D-alpha-tocopherol succinate) | 1-400IU |
| Vitamin E (as D-alpha-tocopherol acetate) | 1-400 IU |
| Vitamin B1 (as thiamine mononitrate) | 1-20 mg |
| Vitamin B2 (as riboflavin) | 1-20 mg |
| Vitamin B3 (as niacinamide) | 1-100 mg |
| Vitamin B5 (as d-calcium pantothenate) | 1-30 mg |
| Vitamin B6 (as pyridoxin HQ) | 1-15 mg |
| Vitamin B7 (Biotin) | 1-500 mcg |
| Vitamin B12 (as methylcobalamine) | 2-20 mcg |
| Folate (as L-5- methyltetrahydrofolate, calcium) | 1-500 mcg |
| Calcium (as citrate) | 5-250 mg |
| Magnesium (as citrate) | 1-250 mg |
| Zinc (as biglycinate chelate) | 1-30 mg |
| Selenium (as selenomethionine) | 1-300 mcg |
| Chromium (as picolinate) | 1-100 mcg |
| N-acetylcysteine | 1-500 mg |
| Coenzyme Q10 | 1-400 mg |
| Alpha-lipoic acid | 1-500 mg |
| Natural Beta carotene | 1-250 mcg RAE |
| Curcumin | 1-500 mg |
| Trans-resveratrol | 1-250 mg |
| Quercetin | 1-200 mg |
| Green tea extract | 1-250 mg |

Humans are being exposed to increased levels of electromagnetic field (EMF) radiation from various wireless communication technologies. Adverse health effects have been reported from exposure to EMF radiation. Introduction of 5G or 5th Generation technology, which transmits signal at frequency range between 3-300 GHz, has raised concerns about increased hazard to human health. No significant human studies on 5G EMF radiation have been performed.

Epidemiologic studies suggest that exposure to EMF radiation increases the risk of certain brain cancer. Animal studies have supported the above conclusion. A few epidemiologic investigations studies have reported that EMF radiation does not increase the risk of cancer. Some potential reasons for this inconsistent results could be that the level of frequency, dose (strength) (voltage per meter or V/m), intensity (millitesla of mT), and energy absorption SAR (specific absorption rate, Watts/Kg of tissue) were not comparable.

EMF radiation induces hypersensitivity in humans, who exhibit neurological syndromes that include fatigue, dizziness, headache, lack of concentration, cognitive impairment, and sleep disturbances. Pre-treatment with individual antioxidants reduced DNA damage, markers of oxidative damage and inflammation, and increased viability of neurons in the brain. Exposure of mammalian cells in culture to EMF radiation reduced cell viability in the brain and testis, and increased chromosomal aberrations. There are no controversies on EMF-induced neurological abnormalities. EMF radiation increases the levels of markers of oxidative damage and inflammation, which contribute to EMF radiation-induced damage.

Because of limitations of physical protection, a novel biological concept of PAMARA (protection as much as reasonable achievable) is proposed. This concept suggests that supplementation with a mixture of micronutrients may reduce EMF radiation-induced acute and late adverse health effects in humans.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

Numerous modifications and variations of the present invention are possible in light of the above teachings. It is therefore to be understood that within the scope of the attendant claims attached hereto, this invention may be practiced otherwise than as specifically disclosed herein.

What is claim is:

1. A formulation comprising at least one vitamin, at least one antioxidant, at least one mineral, at least one plant based nutrient and sodium, wherein
    (a) said at least one vitamin is selected from the group consisting of Vitamin A, Vitamin D3, Vitamin B1, Vitamin B2, Vitamin B3, Vitamin B5, Vitamin B6, Vitamin B7, Vitamin B12, Folate and combinations and mixtures thereof;
    (b) said at least one antioxidant is selected from the group consisting of Vitamin C, D-alpha-tocopherol succinate, D-alpha-tocopherol acetate and combinations and mixtures thereof;
    (c) said at least one mineral is selected from a group consisting of calcium, magnesium, zinc, selenium, chromium, and mixtures and combinations thereof; and
    (d) said at least one plant based nutrient is selected from a group consisting of natural beta carotene, curcumin, trans-resveratrol, quercetin and mixtures and combinations thereof wherein said at least one vitamin, said at least one antioxidant, said at least one mineral, said at least one plant based nutrient, and said sodium are the only therapeutically active agents in said formulation.

2. The formulation of claim 1 wherein the amount of said at least one vitamin in said formulation is from about 1 to about 1,000 IU.

3. The formulation of claim 1 wherein the amount of said at least one antioxidant in said formulation is from about 1 to about 1,000 IU.

4. The formulation of claim 1 wherein the amount of said at least on mineral in said formulation is from about 0.001 to about 500 mg.

5. The formulation of claim 1 wherein the amount of said plant based nutrient in said formulation is from about 1 to 1,000 mg.

6. The formulation of claim 1 wherein a therapeutically effective amount of the formulation is intended to be administered at least once a day.

7. The formulation of claim 1 wherein a therapeutically effective amount of the formulation is intended to be administered at least twice a day.

8. The formulation of claim 1 wherein said formulation is designed to reduce the harmful effects of environmental factors on human health.

9. The formulation of claim 1 wherein said formulation is designed to provide protection to humans from environmental factors.

10. The formulation of claim 1 wherein said formulation is designed to mitigate the harmful effects of environmental factors.

* * * * *